US012274273B2

(12) United States Patent
Hattori et al.

(10) Patent No.: US 12,274,273 B2
(45) Date of Patent: Apr. 15, 2025

(54) WHEY PROTEIN GRANULES

(71) Applicant: MEIJI CO., LTD., Tokyo (JP)

(72) Inventors: Hiroki Hattori, Tokyo (JP); Koji Yamamura, Tokyo (JP); Takashi Osada, Tokyo (JP); Keisuke Kadoyama, Tokyo (JP); Toshiaki Tochigi, Tokyo (JP)

(73) Assignee: MEIJI CO., LTD., Tokyo (JP)

( * ) Notice: Subject to any disclaimer, the term of this patent is extended or adjusted under 35 U.S.C. 154(b) by 460 days.

(21) Appl. No.: 17/761,710

(22) PCT Filed: Sep. 18, 2020

(86) PCT No.: PCT/JP2020/035525
§ 371 (c)(1),
(2) Date: Mar. 18, 2022

(87) PCT Pub. No.: WO2021/054452
PCT Pub. Date: Mar. 25, 2021

(65) Prior Publication Data
US 2022/0394990 A1    Dec. 15, 2022

(30) Foreign Application Priority Data

Sep. 20, 2019  (JP) ................. 2019-172258

(51) Int. Cl.
*A23C 21/00*  (2006.01)
*A23J 1/20*  (2006.01)
*A23J 3/08*  (2006.01)
*A23P 10/22*  (2016.01)

(52) U.S. Cl.
CPC ............... *A23C 21/00* (2013.01); *A23J 1/205* (2013.01); *A23J 3/08* (2013.01); *A23P 10/22* (2016.08)

(58) Field of Classification Search
CPC . A23C 21/00; A23P 10/22; A23J 1/205; A23J 3/08
USPC ........................................ 426/583
See application file for complete search history.

(56) References Cited

U.S. PATENT DOCUMENTS

2009/0098274 A1  4/2009  Kodama et al.
2017/0156369 A1  6/2017  Liu et al.

FOREIGN PATENT DOCUMENTS

| CA | 3 131 072 | 8/2020 |
| JP | 5-220377 | 8/1993 |
| JP | H 5220377 A * | 8/1993 |
| JP | 2007-209230 | 8/2007 |
| JP | 2016-116494 | 6/2016 |

(Continued)

OTHER PUBLICATIONS translation of JPH 5220377A (Year: 1993).*

(Continued)

*Primary Examiner* — Brent T O'Hern
(74) *Attorney, Agent, or Firm* — Wenderoth, Lind & Ponack, L.L.P.

(57) ABSTRACT

An embodiment of the present invention relates to protein granules containing a whey protein as a main component, the protein granules having an average particle diameter of 207 μm to 570 μm, a homogeneity U of 0.58 or less, a content ratio (volume ratio) of coarse powder having a particle diameter of 500 μm or more of 22% or less, and a content ratio (volume ratio) of fine powder having a particle diameter of 150 μm or less of 31% or less.

20 Claims, 3 Drawing Sheets

(56) References Cited

FOREIGN PATENT DOCUMENTS

| | | | |
|---|---|---|---|
| JP | 2016116494 A | * | 6/2016 |
| JP | 2017-88527 | | 5/2017 |
| JP | 2017-136549 | | 8/2017 |
| JP | 2017-521498 | | 8/2017 |
| WO | 2007/123113 | | 11/2007 |
| WO | 2015/146880 | | 10/2015 |
| WO | 2018/174051 | | 9/2018 |
| WO | 2020/171068 | | 8/2020 |

OTHER PUBLICATIONS translation of JP-2016116494-A (Year: 2016).*
Notification of First Office Action issued Jul. 22, 2023 in corresponding Chinese Patent Application No. 202080065691.7, with English language translation.
Office Action issued Apr. 4, 2024 in Chinese Patent Application No. 202080065691.7, with English-language Translation.
Office Action issued Jun. 5, 2024, in corresponding Taiwanese Patent Application No. 109132457, with English-language Translation.
International Search Report issued Dec. 1, 2020 in International (PCT) Application No. PCT/JP2020/035525.
Notice of Reasons for Refusal issued Jul. 9, 2024, in corresponding Japanese Patent Application No. 2021-546987, with English-language translation.
Decision of Refusal issued Feb. 12, 2025 in corresponding Japanese Patent Application No. 2021-546987, with English language translation.

* cited by examiner

WHEY PROTEIN GRANULES

TECHNICAL FIELD

The present invention relates to protein granules, and more particularly to protein granules containing a whey protein as a main component.

BACKGROUND ART

A whey protein is a protein contained in whey obtained by removing casein and the like from milk, and examples of the whey protein include lactalbumin, lactalbumin, and lactoferrin.

The whey protein is used as a protein supply source for an exercise nutritional food, a diet food, and the like. However, when the whey protein is dissolved in water as it is, a surface of a powder mass becomes candy-like to cause a clump or a lump. Once a clump is formed, it becomes difficult to dissolve the whey protein unless the clump is carefully crushed.

In general, in enhancing water solubility of a powder raw material, a method of granulating the powder raw material into granules for improving the settleability and allowing the powder raw material to be easily dispersed or dissolved in water is known. However, when a whey protein is present at a high concentration in the powder raw material, the settleability in water is still poor even when the powder raw material is granulated, and it is difficult to improve the solubility in water. Thus, a large amount of undissolved proteins remain, and undissolved candy-like proteins may adhere to an oral cavity in oral ingestion. This makes it difficult to swallow such a thing.

In order to solve the above problem, for example, Patent Literature 1 proposes that generation of a clump can be suppressed in a whey protein-containing granule by using, as an emulsifier, a polyglycerol fatty acid ester containing lauric acid having HLB of 13 to 18 as a constituent fatty acid. However, this method still does not sufficiently improve the water solubility of the whey protein.

CITATION LIST

Patent Literature

Patent Literature 1: WO2007/123113

SUMMARY OF INVENTION

Technical Problem

Accordingly, an object of the present invention is to provide whey protein granules having sufficiently high water solubility. Another object of the present invention is to provide whey protein granules that are sufficiently dissolved in water and are capable of preparing a protein solution having less undissolved protein and being easily swallowed.

Solution to Problem

As a result of intensive studies, the present inventors have found that the above problems can be solved, in protein granules containing a whey protein as a main component, by setting an average particle diameter and a homogeneity U defined below to a specific range, and adjusting a content ratio of a coarse powder and a fine powder to a specific range, and have completed the present invention.

That is, the present invention is as follows.

[1] Protein granules containing a whey protein as a main component in which the protein granules have an average particle diameter of 207 μm to 570 μm, a homogeneity U of 0.58 or less, a content ratio (volume ratio) of a coarse powder having a particle diameter of 500 μm or more of 22% or less, and a content ratio (volume ratio) of a fine powder having a particle diameter of 150 μm or less of 31% or less, and in which the average particle diameter, the homogeneity U, the content ratio (volume ratio) of the coarse powder having a particle diameter of 500 μm or more, and the content ratio (volume ratio) of the fine powder having a particle diameter of 150 μm or less, are determined by the following measurement method:

[Method for Measuring Average Particle Diameter, Homogeneity U, and Content Ratio of Coarse Powder and Fine Powder]

1. a volume-based particle size distribution in which data is plotted with the particle diameter as a horizontal axis and with the content ratio of particles as a vertical axis is obtained for the granules by a laser diffraction and scattering measurement method,
2. the average particle diameter and the content ratio of the coarse powder and the content ratio of the fine powder are determined from the volume-based particle size distribution, and
3. the homogeneity U is determined by the following formula (1).

[Formula 1]

$$U = \frac{\sum X_i |D_i - D_p|}{D_p} \quad (1)$$

In the formula (1), $D_p$ is an average particle diameter (μm), $X_i$ is a content ratio of particles at each particle diameter in the volume-based particle size distribution, and $D_i$ is a particle diameter (μm) of each particle.

[2] The protein granules according to [1], in which the protein granules have a protein content of 50 mass % or more.

[3] The protein granules according to [1] or [2], in which the protein granules have the average particle diameter of 260 μm to 330 μm.

[4] The protein granules according to any one of [1] to [3], in which the protein granules have the homogeneity U of 0.36 to 0.47.

[5] The protein granules according to any one of [1] to [4], in which the protein granules have the content ratio (volume ratio) of the coarse powder having a particle diameter of 500 μm or more of 11% or less, and the content ratio (volume ratio) of the fine powder having a particle diameter of 150 μm or less of 17% or less.

[6] The protein granules according to any one of [1] to [5], in which a residue weight of the granules is 1 g or less, when 7 g of the granules is added to 100 ml of water and stirred, then the mixture is sieved with a sieve having a size of mesh opening of 500 μm, and granules remaining on the sieve are dried at 98° C. for 4 hours.

[7] The protein granules according to any one of [1] to [6], further including: at least one selected from the group consisting of a carbohydrate, a vitamin, an emulsifier, and a thickening polysaccharide.

[8] A food or drink, including: the protein granules according to any one of [1] to [7].

[9] A whey protein-containing food or drink obtained by dissolving the food or drink according to [8] in a water-containing substance.

[10] A method for producing the protein granules according to any one of [1] to [7], including: a mixing step of mixing a whey protein powder and other components; and a granulation step of granulating the mixture obtained in the mixing step.

[11] The production method according to [10], further including: a step of classifying the granules obtained in the granulation step by sieving.

Advantageous Effects of Invention

The present invention allows for providing protein granules having sufficiently high water solubility, as the protein granules has the average particle diameter, the homogeneity U, and the content ratio of the coarse powder and the fine powder within the specific ranges. The present invention allows for providing a whey protein granules capable of preparing a protein solution having less undissolved protein and being easily swallowed.

DESCRIPTION OF EMBODIMENTS

Figure 1:
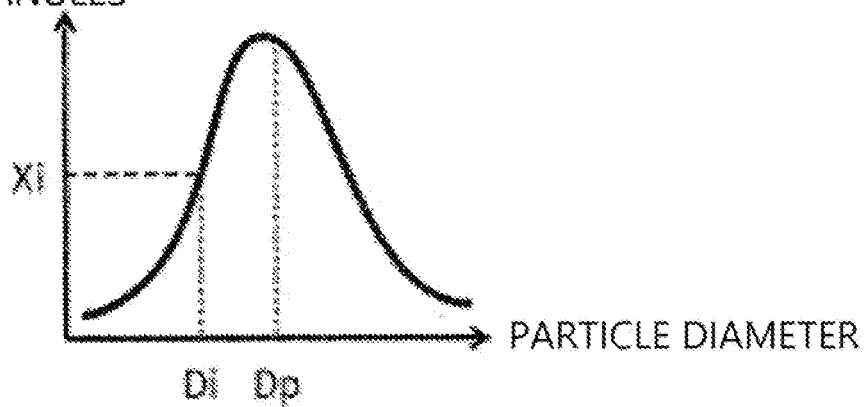
FIG. 1 is a graph for illustrating a homogeneity U.

Hereinafter, an embodiment of the present invention will be described in more detail.

An embodiment of the present invention is protein granules containing a whey protein as a main component, and having an average particle diameter, a homogeneity U, and a content ratio of a coarse powder and a fine powder within specific ranges. In the protein granules of the present embodiment (hereinafter, may be simply referred to as granules), setting the average particle diameter, the homogeneity U, and the content ratio of the coarse powder and the fine powder to specific ranges allows for providing protein granules having sufficiently high water solubility.

In the present embodiment, the reason why sufficiently high water solubility is imparted by adjusting the average particle diameter, the homogeneity U, and the content ratio of the coarse powder and the fine powder to specific ranges is not clear at present, but it is presumed that the possible reason is as follows. That is, the fine powder having a small particle diameter becomes clump in water and the clump is not settled, and the coarse powder having a large particle diameter does not allow water to penetrate into the inside and remains undissolved. Therefore, the solubility in water can be improved by setting the content ratio of the fine powder or the coarse powder to a certain value or less and adjusting the average particle diameter or the homogeneity to a specific range. It should be noted that the present embodiment is not limited to the one that exhibits the above-described effects.

The whey protein in the present embodiment is a generic term for proteins excluding casein in milk. The protein may be classified as a whey protein. The whey protein is composed of two or more components such as lactoglobulin, lactalbumin, and lactoferrin, and does not contain lactose, vitamin, mineral, and the like. When a milk raw material such as milk is made to be acidic, a precipitated protein is casein, and a non-precipitated protein is a whey protein.

For the granules according to the present embodiment, for example, a powder raw material containing a whey protein can be used as a raw material. Examples of the powder raw material containing a whey protein include a whey protein concentrate (WPC, protein content: 75 mass % to 85 mass %) and a whey protein isolate (WPI, protein content: 85 mass % or more). These may be used alone or in combination.

The granules according to the present embodiment contain a whey protein as a main component. Here, the "main component" means a component having the highest content ratio (on a mass basis) among all the components of the granules. A content of the whey protein in the granules is preferably 50 mass % or more, more preferably 55 mass % or more, still more preferably 60 mass % or more, yet still more preferably 65 mass % or more, and particularly preferably 68 mass % or more, with respect to the granules.

When the content of the whey protein in the granules is within the above range, the granules with high purity of the protein is obtained. The granules according to the present embodiment have sufficiently high water solubility, and thus, even such a high-concentration protein can be dissolved in water.

An upper limit of the content of the whey protein in the granules according to the present embodiment is not limited, but is, for example, 99 mass % or less, 95 mass % or less, or 90 mass % or less, with respect to the granules.

The granules according to the present embodiment needs to have an average particle diameter of 207 μm to 570 μm. When the average particle diameter is within the above range, the solubility of the granules in water becomes sufficiently high, and a protein solution having less undissolved protein and being easily swallowed can be prepared.

The average particle diameter of the granules is preferably 230 μm or more, more preferably 240 μm or more, still more preferably 250 μm or more, and particularly preferably 260 μm or more.

The average particle diameter of the granules is preferably 500 μm or less, more preferably 450 μm or less, even more preferably 400 μm or less, still more preferably 350 μm or less, yet still more preferably 330 μm or less, and particularly preferably 300 μm or less.

The average particle diameter of the granules according to the present embodiment can be determined from a volume-based particle size distribution in which data is plotted with the particle diameter as a horizontal axis and with the content ratio of particles as a vertical axis, obtained by a laser diffraction and scattering measurement method, as shown in FIG. 1. Specifically, the average particle diameter can be determined from the volume-based particle size distribution based on the following formula.

[Formula 2]

$$D_p = \frac{\sum_{i=1}^{n} X_i * D_i^4}{\sum_{i=1}^{n} X_i * D_i^3}$$

In the above formula, $D_p$ is an average particle diameter (μm), $D_i$ is any particle diameter (μm), and $X_i$ is a content ratio (volume ratio) of particles of the granules at $D_i$. Here, the content ratio (volume ratio) of particles of the granules at $D_i$ means a ratio of a volume of the granules having the particle diameter $D_i$ to a volume of the entire granules, and means $V_i/V$ where V is the volume of the entire granules, and $V_i$ is the volume of the granules having the particle diameter $D_i$.

In the present embodiment, a median diameter of a volume-based frequency distribution can be measured using a laser diffraction and scattering particle size distribution measuring device, and the median diameter can be defined as an average particle diameter. As the laser diffraction and scattering particle size distribution measuring device, for example, Mastersizer 3000 (trade name) manufactured by Malvern Co., Ltd. and the included soft Mastersizer 3000 can be used.

The granules according to the present embodiment needs to have a homogeneity U of 0.58 or less. The homogeneity U refers to a value represented by the following formula (1), and when the value is low, granules in which the particle size distribution of the granules is sharp is obtained. When the homogeneity U is within the above range, the solubility of the granules in water becomes sufficiently high, and a protein solution having less undissolved protein and being easily swallowed can be prepared.

The homogeneity U of the granules according to the present embodiment is preferably 0.55 or less, more preferably 0.50 or less, still more preferably 0.47 or less, and particularly preferably 0.40 or less. A lower limit value of the homogeneity U of the granules is, for example, 0.25 or more, 0.30 or more, or 0.36 or more.

The homogeneity U of the granules according to the present embodiment can be measured using the Mastersizer 3000 (trade name) manufactured by Malvern Co., Ltd. and the included soft Mastersizer 3000 as the laser diffraction and scattering particle size distribution measuring device, in the similar manner to the measurement of the average particle diameter described above.

Hereinafter, the homogeneity U will be described with reference to FIG. 1. In FIG. 1, when $D_p$ is defined as an average particle diameter (μm), which is a median diameter of a volume-based frequency distribution, and $D_i$ is defined as an particle diameter (μm) of any particles of the granules, a content ratio (volume ratio) of the particles of the granules at $D_i$ is represented by $X_i$. The particle size distribution of the particles of the granules, that is, the homogeneity U can be expressed by the following formula (1). A numerator of formula (1) is a sum of values obtained by multiplying a difference between the particle diameter $D_i$ and the average particle diameter $D_p$ of any particles by the content ratio $X_i$, and the homogeneity U is a value obtained by dividing the sum by the average particle diameter $D_p$.

In formula (1), the symbol "||" represents an absolute value. The content ratio (volume ratio) of the particles of the granules in $D_i$ means a ratio of the volume of the granules having the particle diameter $D_i$ to the volume of the entire granules, and means $V_i/V$ where V is the volume of the entire granules, and $V_i$ is the volume of the granules having the particle diameter $D_i$.

[Formula 3]

$$U = \frac{\sum X_i |D_i - D_p|}{D_p} \quad (1)$$

As can be seen from the above formula (1), the sharper particle size distribution of the particles of the granules equates to the lower value of the homogeneity U. In the present embodiment, as described above, the homogeneity U needs to be 0.58 or less, and it can be said that the particle size distribution is narrow.

The granules according to the present embodiment needs to have the content ratio (volume ratio) of the coarse powder having a particle diameter of 500 μm or more of 22% or less. When the content ratio of the coarse powder is within the above range, the solubility of the granules in water becomes sufficiently high, and a protein solution having less undissolved protein and being easily swallowed can be prepared.

The content ratio (volume ratio) of the coarse powder having a particle diameter of 500 μm or more is preferably 20% or less, more preferably 18% or less, still more preferably 16% or less, yet still more preferably 14% or less, and particularly preferably 11% or less.

The content ratio (volume ratio) of the coarse powder having a particle diameter of 500 μm or more is, for example, 4% or more, 8% or more, or 10% or more.

The granules according to the present embodiment needs to have the content ratio (volume ratio) of the fine powder having a particle diameter of 150 μm or less of 31% or less. When the content ratio of the fine powder is within the above range, the solubility of the granules in water becomes sufficiently high, and a protein solution having less undissolved protein and being easily swallowed can be prepared.

The content ratio (volume ratio) of the fine powder having a particle diameter of 150 μm or less is preferably 28% or less, more preferably 25% or less, still more preferably 22% or less, yet still more preferably 17% or less, and particularly preferably 12% or less.

The content ratio (volume ratio) of the fine powder having a particle diameter of 150 μm or less is, for example, 7% or more, 10% or more, or 11% or more.

The content ratio (volume ratio) of the coarse powder and the fine powder can be determined from the volume-based particle size distribution obtained by the laser diffraction and scattering measurement method in which data is plotted with the particle diameter as a horizontal axis and with the content ratio of particles as a vertical axis, as shown in FIG. 1.

Specifically, the content ratio (volume ratio) of the coarse powder having a particle diameter of 500 μm or more can be determined from the volume-based particle size distribution based on the following formula.

[Formula 4]

$$X_l = \frac{\sum_{k=1}^{b} X_k * D_k^3}{\sum_{i=1}^{n} X_i * D_i^3} \times 100$$

In the above formula, $X_l$ is the content ratio (volume ratio (%)) of the coarse powder, $D_k$ is any particle diameter (μm) of 500 μm or more, and $X_k$ is the content ratio (volume ratio) of particles at the particle diameter $D_k$. $X_i$ and $D_i$ are the same as in the above formula (1). The content ratio (volume ratio) of the particles at the particle diameter $D_k$ means the ratio of the volume of the granules having the particle diameter $D_k$ to the volume of the entire granules, and means $V_k/V$ where V is the volume of the entire granules, and $V_k$ is the volume of the granules having the particle diameter $D_k$.

The content ratio (volume ratio) of the fine powder having a particle diameter of 150 μm or less can be determined from the volume-based particle size distribution based on the following formula.

[Formula 5]

$$X_s = \frac{\sum_{j=1}^{a} X_j * D_j^3}{\sum_{i=1}^{n} X_i * D_i^3} \times 100$$

In the above formula, $X_s$ is the content ratio (volume ratio (%)) of the fine powder, $D_j$ is any particle diameter (μm) of 150 μm or less, and $X_j$ is the content ratio (volume ratio) of particles at the particle diameter $D_j$. $X_i$ and $D_i$ are the same as in the above formula (1). The content ratio (volume ratio) of the particles at the particle diameter $D_j$ means the ratio of the volume of the granules having the particle diameter $D_j$ to the volume of the entire granules, and means $V_j/V$, where V is the volume of the entire granules, and $V_j$ is the volume of the granules having the particle diameter $D_j$.

The granules according to the present embodiment may contain a protein other than the whey protein. Examples of the protein other than whey protein include a collagen protein, a milk protein, a milk protein concentrate (MPC), a soy protein, a wheat protein, a wheat protein hydrolyzate, and a whey peptide. These may be used alone or in combination.

The content of all proteins in the granules according to the present embodiment is preferably 50 mass % or more, more preferably 55 mass % or more, still more preferably 60 mass % or more, yet still more preferably 65 mass % or more, and particularly preferably 68 mass % or more, with respect to the granules.

An upper limit of the content of all proteins in the granules according to the present embodiment is not limited, but is, for example, 99 mass % or less, 95 mass % or less, or 90 mass % or less, with respect to the granules. The granules according to the present embodiment can have sufficient high water solubility even when containing a large amount of protein as described above.

The granules according to the present embodiment can contain components other than the protein as long as the effects of the present invention are not impaired. The other components are not limited, and may be appropriately selected from those known in the art depending on the intended use.

As described above, in the granules according to the present embodiment, sufficiently high water solubility is imparted by adjusting the average particle diameter, the homogeneity U, and the content ratio of the coarse powder and the fine powder to specific ranges. It is presumed that this is because the fine powder having a small particle diameter floats on a water surface and is difficult to be settled in water, and even when the fine powder is settled, a clump is formed and the clump is difficult to disperse, and the coarse powder having a large particle diameter does not allow water to penetrate into the inside and remains undissolved. From the above, it is important to adjust the content ratio of the fine powder and the coarse powder to a certain value or less and adjust the average particle diameter and the homogeneity to a specific range, for improving the solubility of the granules in water. Therefore, even when the granules contains other components other than the protein, the solubility of the granules in water can be improved by adjusting the average particle diameter, the homogeneity U, and the content ratio of the coarse powder and the fine powder to specific ranges.

Examples of the other components include, as a binder, thickening polysaccharides such as pullulan, gum arabic, guar gum, xanthan gum, and locust bean gum. When the granules contain a binder, the content of the binder is preferably 0.05 mass % to 1 mass %, more preferably 0.1 mass % to 0.8 mass %, and still more preferably 0.1 mass % to 0.6 mass %, with respect to the granules, from the viewpoint of allowing the particles to bond to each other and from the viewpoint of improvement in solubility.

Examples of the carbohydrates include sucrose, glucose, maltose, fructose, lactose, erythritol, trehalose, sorbitol, maltitol, xylitol, oligosaccharide, dextrin, maltodextrin, and soluble starch. When the granules contain carbohydrates, the content of the carbohydrates is preferably 0 to 50 mass %, more preferably 0 to 35 mass %, and still more preferably 0 to 20 mass %, with respect to the granules, from the viewpoint of nutritional design.

Examples of an acidulant include citric acid, malic acid, tartaric acid, and lactic acid. When the granules contain an acidulant, the content of the acidulant is preferably 1 mass % to 20 mass %, more preferably 2 mass % to 15 mass %, and still more preferably 3 mass % to 10 mass %, with respect to the granules, from the viewpoint of nutritional design, and improvement in flavor and palatability.

Examples of a sweetener include stevia, aspartame, sucralose, and acesulfame potassium. When the granules contain a sweetener, the content of the sweetener is preferably 0 to 1 mass %, more preferably 0.01 mass % to 1 mass %, and still more preferably 0.02 mass % to 0.5 mass %, with respect to the granules, from the viewpoint of improvement in flavor and palatability.

Examples of a mineral include calcium, magnesium, potassium, iron, sodium, and zinc. When the granules contain a mineral, the content of the mineral is preferably 0 to 6 mass %, more preferably 0.1 mass % to 4 mass %, and still more preferably 0.2 mass % to 2 mass %, with respect to the granules, from the viewpoint of nutritional design, and improvement in flavor and palatability.

Examples of a vitamin include fat-soluble vitamins A, D, E, and K, water-soluble vitamins B group (B1, B2, B6, B12, and the like), vitamin C, pantothenic acid, folic acid, and niacin. When the granules contain a vitamin, the content of the vitamin is preferably 0 to 5 mass %, more preferably 0.1 mass % to 3 mass %, and still more preferably 0.2 mass % to 1.5 mass %, with respect to the granules, from the viewpoint of nutritional design, and improvement in flavor and palatability.

Examples of an amino acid include valine, leucine, isoleucine, glutamine, lysine, and methionine. When the granules contain an amino acid, the content of the amino acid is preferably 0 to 20 mass %, more preferably 0.1 mass % to 10 mass %, and still more preferably 1 mass % to 5 mass %, with respect to the granules, from the viewpoint of nutritional design, and improvement in flavor and palatability.

Examples of a fragrance include vanilla fragrance, milk fragrance, fruit fragrance, and drink fragrance. When the granules contain a fragrance, the content of the fragrance is preferably 0.1 mass % to 4 mass %, more preferably 0.3 mass % to 3 mass %, and still more preferably 0.5 mass % to 2.5 mass %, with respect to the granules, from the viewpoint of improvement in flavor and palatability.

Examples of an emulsifier include a monoglycerol fatty acid ester, a polyglycerol fatty acid ester, a sucrose fatty acid ester, a sorbitan fatty acid ester, a propylene glycol fatty acid ester, a monoglycerol organic acid ester, and a monoglycerol phosphoric acid ester. When the granules contain an emulsifier, the content of the emulsifier is preferably 0 to 3 mass %, more preferably 0 to 2.5 mass %, and still more preferably 0 to 1.5 mass %, with respect to the granules, from the viewpoint of improvement in solubility and flavor.

These other components may be used alone or in combination.

In particular, the granules according to the present embodiment preferably contain carbohydrates, vitamins, an emulsifier, and thickening polysaccharides.

An embodiment of the present invention is a powder food or drink containing the protein granules. The other components are not limited as long as the powder food or drink according to the present embodiment contains the protein granules described above, and may be appropriately selected from known components according to the intended use.

Another embodiment of the present invention is a whey protein-containing food or drink obtained by dissolving the powder food or drink in a water-containing substance. Since the granules or the powder food or drink has good water solubility, the granules or the powder food or drink can be sufficiently dissolved in a water-containing substance.

The water-containing substance is not limited, but examples of the water-containing substance include water, milk, dairy products such as yogurt, whey beverage, milk beverage, and processed milk, fruit juice, vegetable juice, and alcoholic beverage.

The granules, the powder food or drink, and the whey protein-containing food or drink according to the present embodiment can be in a form of a health food, a specific health food, a nutritional functional food, a supplement, a food with functional claims, a medicine, and the like, for replenishing whey protein. The granules, the powder food or drink, and the whey protein-containing food or drink according to the present embodiment contain the whey protein at a high concentration, and thus, these products allows for reducing the intake of the product at one time. In addition, the granules according to the present embodiment have good water solubility, and thus, a consumer can easily take the granules.

The granules according to the present embodiment are granulated so as to satisfy the average particle diameter, the homogeneity U, and the content ratio of the coarse powder and the fine powder in specific ranges. Those skilled in the art can set the average particle diameter, the homogeneity U, and the content ratio of the coarse powder and the fine powder in the specific ranges by appropriately selecting various conditions using a common known mixing method or granulation method described below.

The granules according to the present embodiment can be produced through a step of mixing a whey protein powder and other components, and a step of granulating the obtained mixture. Such a production method may include a step of classifying the granules obtained in the granulation step by sieving. The details will be described below.

For obtaining the granules according to the present embodiment, first, the whey protein powder is mixed with other optional components as necessary. The mixing method is not limited, and can be performed by a method typically used in the related art. For example, a horizontal cylinder type mixer, a V type mixer, a double cone type mixer, a swing rotation type mixer, a single axis ribbon type mixer, a double axis paddle type mixer, a rotating operation type mixer, a conical screw type mixer can be used for the mixing. In addition, granulation may be performed simultaneously with mixing of various components in the granulation process described below.

Subsequently, the mixture obtained as described above can be granulated by a typical granulation method. The granulation method is not limited. Both of dry granulation and wet granulation can be used. Examples of the dry granulation include a slag method and a roller compactor method. Examples of the wet granulation include stirring and mixing granulation, spray drying granulation, fluidized bed granulation, tumbling granulation, tumbling fluidized bed granulation, and extrusion granulation.

The stirring and mixing granulation is a granulation method in which water and a binder are added to stirred particles, followed by shearing, tumbling, and compacting actions by rotation of blades having various shapes to proceed with crosslinking formation between the particles, to repeat generation, bonding (association) and crushing (dissociation) of fine particles and to cause growth of the particles to form granulated particles.

The spray drying granulation is a granulation method in which a liquid is dispersed and dried in a high-temperature air stream.

The fluidized bed granulation is a granulation method in which powder is coagulated and granulated with water and a binder sprayed while a powder layer is kept in a fluidized state on a fluidized bed such as a normal fluidized bed, a circulating fluidized bed, a forced circulating fluidized bed, or a spouted bed.

The tumbling granulation is a granulation method in which raw material powders of particles are tumbled in various containers by the action of stirring blades with water and a binder sprayed to form fine particles by crosslinking formation between particles, and the growth of the particles is promoted by applying tumbling and rotating motions to the particles. The tumbling granulation is performed using a dish-type (ban-type) granulator, a drum-type granulator, a vibration-type granulator, or the like.

The tumbling fluidized bed granulation is a mechanism having the characteristics of both the stirring granulation and the fluidized bed granulation and is a granulation method in which granulated particles are formed by tumbling, flowing, and stirring particles with water and a binder sprayed to advance the crosslinking formation between the particles.

The extrusion granulation refers to granulating powder by mixing and kneading it with water and a binder added, and extruding a plasticized powder from a screen or die having a large number of holes with a screw, a roller, or the like. The extrusion granulation is performed using a front extrusion granulator, a disc pelleter granulator, a ring die granulator, a basket granulator, an oscillating granulator, a cylinder granulator, or the like.

In the wet granulation, for example, when a fluidized bed granulation method is adopted, a common known fluidized bed granulation device can be used. In this device, a fluid such as air is blown up from a lower portion of the device, solid particles (raw material powders) are allowed to float (flowing), and a spray liquid such as water or a binder is sprayed on the solid particles to perform granulation and drying. A commercially available fluidized bed granulator can be used as the fluidized bed granulator. Examples of the operation conditions to be adjusted at this time include a type of the spray liquid, a spray liquid amount, a spray flow rate, a blowing air amount, a blowing air temperature, an exhaust air temperature, and a damper opening degree.

As the binder, those typically used in the related art can be used. Examples of the binder include cellulose derivatives such as methyl cellulose, hydroxypropyl cellulose, hypromellose, and hypromellose phthalate; starches such as corn starch and wheat starch; synthetic polymers such as polyvinyl pyrrolidone and acrylic acid polymers; and natural polymers such as gum arabic and gelatin. These may be used alone or in combination. The amount of the binder to be used can be limited to an extent that normal granulation is possible.

For example, when granulation is performed by fluidized bed granulation, the specific average particle diameter, homogeneity U, and content ratio of the coarse powder and the fine powder in the present embodiment can be specifically realized by appropriately adjusting a supply air flow rate, a supply air temperature, a binder flow rate, a binder liquid droplet diameter, and the like.

Hereinafter, specific granulation conditions in the case of using a fluidized bed granulator will be exemplified.

Size at time of introduction of whey protein: 180 μm to 220 μm

Amount at time of introduction of whey protein: 200 g to 600 g

Supply air temperature (granulation): 50° C. to 100° C.

Supply air temperature (drying): 50° C. to 100° C.

Supply air flow rate (granulation): 0.2 m³/min to 0.8 m³/min

Supply air flow rate (drying): 0.2 m³/min to 0.8 m³/min

Binder flow rate: 10 g/min to 50 g/min

Amount of binder to be added: 30 g to 500 g

Spray air flow rate: 10 L/min to 40 L/min

Granulation time: 3 minutes to 60 minutes

If necessary, the granules obtained as described above may be further classified by sieving, and the average particle diameter, the homogeneity U, and the content ratio of the coarse powder and the fine powder of the granules may be adjusted within the range specified in the present invention.

The granules according to the present embodiment obtained in this manner have sufficient high water solubility, and this allows for easily swallowing in oral ingestion. For example, a residue weight (dry weight) of the granules is 1 g or less, preferably 0.8 g or less, more preferably 0.7 g or less, and still more preferably 0.5 g or less, when 7 g of the granules is added to a container containing 100 ml of water, the mixture is stirred and then sieved with a sieve having a size of mesh opening of 500 μm, and granules remaining on the sieve are dried at 98° C. for 4 hours. When the residue weight of the granules is within the above range, the amount of undissolved protein is small, and thus, this allows for easily swallowing.

EXAMPLE

Hereinafter, the present invention will be further described with reference to Examples and Comparative Examples, but the present invention is not limited to the following Examples.

[Measurement Method]

A measurement method used in the present example will be described below.

[Average Particle Diameter, Homogeneity U, Content Ratio of Coarse Powder and Fine Powder]

A volume-based particle size distribution was obtained by using Mastersizer 3000 (manufactured by Malvern Co., Ltd.) and the included soft Mastersizer 3000, as a laser diffraction and scattering particle size distribution measuring device. The data was plotted with a particle diameter as a horizontal axis and with a content ratio of particles as a vertical axis. For the measurement conditions, a hopper gap was set to 3.5 mm, a feeder strength was set to 20% to 40%, and an air pressure of powder conveyance was set to 0.2 bar.

From the obtained volume-based particle size distribution, an average particle diameter (median diameter), a content ratio of a coarse powder having a particle diameter of 500 μm or more and a fine powder having a particle diameter of 150 μm or less were determined. A homogeneity U was determined from the following formula (1) based on the obtained volume-based particle size distribution.

[Formula 6]

$$U = \frac{\sum X_i |D_i - D_p|}{D_p} \quad (1)$$

In the formula (1), $D_p$ is an average particle diameter (μm), $X_i$ is a content ratio of particles at each particle diameter in the volume-based particle size distribution, and $D_i$ is a particle diameter (μm) of each particle.

Production Example 1

The following components were mixed to prepare a whey protein-containing composition 1 before granulation.

WPC80 (manufactured by Eeprino Foods Company, whey protein content: 78 mass %)

Maltodextrin

Vitamin mixture (containing vitamin A, B1, B2, B6, B12, C, D, E, K, pantothenic acid, folic acid, and niacin)

The prepared composition 1 was introduced into a fluidized bed granulator together with an emulsifier (polyglycerol fatty acid ester) as a liquid component (binder) and an aqueous solution of thickening polysaccharides (pullulan and gum arabic) to obtain granules having a composition shown in Table 1. Note that eight types of granules A to H shown in Table 2 were obtained by changing the amount of the binder to be added, a spray air flow rate, and the like.

A particle diameter of the composition 1 before granulation was set to 180 μm to 220 μm, and a granulation time was set to 10 minutes.

Subsequently, the water solubility of the obtained granules A to H was evaluated by the following method.

7 g of the granules was added to a 300 ml beaker containing 100 ml of water at 25° C., the mixture was stirred for 10 seconds at a peripheral speed of 0.25 m/sec by a stirrer, the granules after stirring were sieved with a sieve having a size of mesh opening of 500 μm, granules remaining on the sieve were dried at 98° C. for 4 hours by a thermostat, and a residue weight (dry weight) was measured to evaluate the water solubility.

Figure 2:
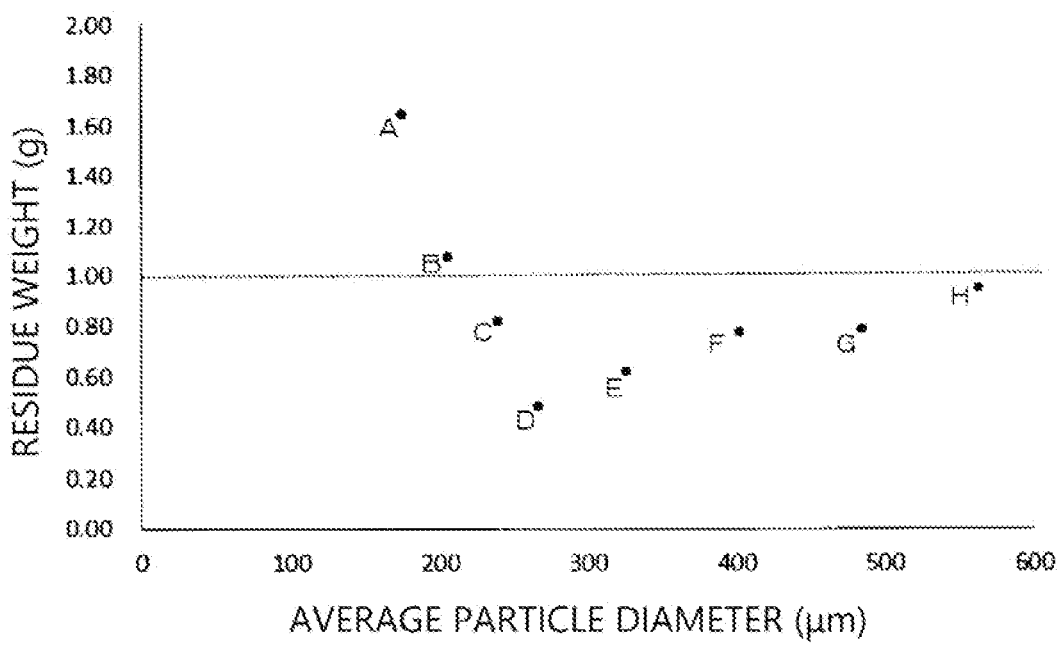
FIG. 2 is a graph illustrating a relationship between an average particle diameter and a residue weight in Production Example 1, in which a horizontal line in FIG. 2 indicates that the residue weight is 1 g.

The results are shown in Table 2 and FIG. 2.

TABLE 1

| Raw materials | Blending ratio (mass %) |
| --- | --- |
| WPC80 | 89.33 |
| Maltodextrin | 8.66 |
| Vitamin mixture | 0.82 |
| Emulsifier | 1.03 |
| Thickening polysaccharide | 0.15 |
| Total | 100 |

TABLE 2

Production Example 1

| Granule | Average particle diameter (μm) | Residue weight (g) |
| --- | --- | --- |
| A | 174 | 1.65 |
| B | 205 | 1.08 |
| C | 238 | 0.82 |
| D | 265 | 0.48 |
| E | 325 | 0.62 |
| F | 401 | 0.78 |
| G | 484 | 0.79 |
| H | 562 | 0.96 |

From the results of Table 2 and FIG. 2, it was found that the residue weight was 1 g or less in the granules C to H having an average particle diameter in a range of 207 μm to 570 μm, and the granules C to H exhibited excellent water solubility.

Production Example 2

In Production Example 2, average particle diameters were roughly equalized, and a difference in a residue weight due to the homogeneity U was confirmed.

The composition 1 prepared in Production Example 1 was introduced into a fluidized bed granulator together with an emulsifier as a liquid component (binder) and an aqueous solution of thickening polysaccharides, and five types of granules I to M shown in Table 3 were obtained by changing the amount of the binder to be added, a spray air flow rate, and the like.

In addition, the obtained granules I to M were evaluated for water solubility in the same manner as in Production Example 1.

Figure 3:
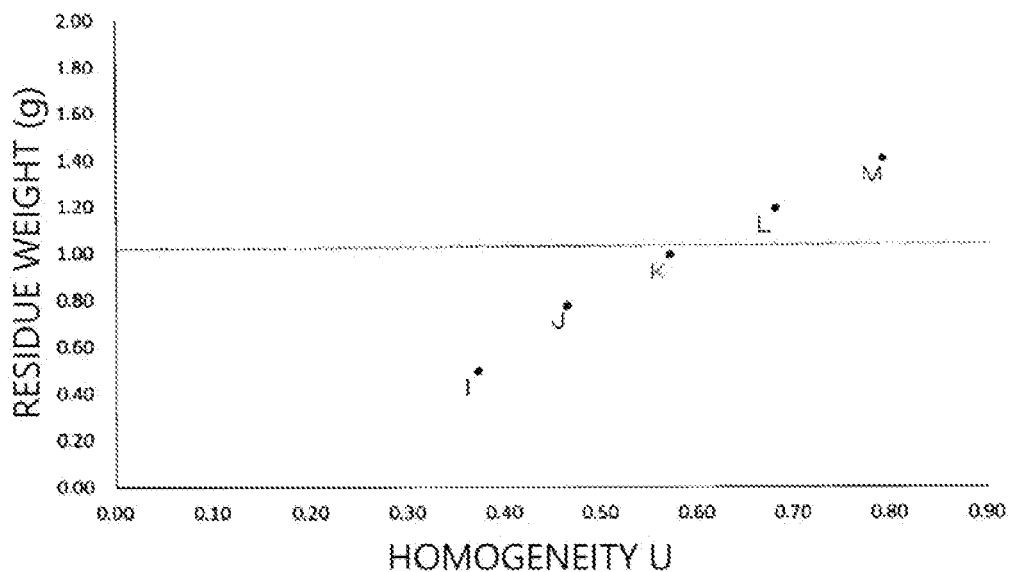
FIG. 3 is a graph illustrating a relationship between a homogeneity U and a residue weight in Production Example 2, in which a horizontal line in FIG. 3 indicates that the residue weight is 1 g.

The results are shown in Table 3 and FIG. 3.

TABLE 3

Production Example 2

| Granule | Average particle diameter (μm) | Homogeneity U | Residue weight (g) |
| --- | --- | --- | --- |
| I | 265 | 0.371 | 0.50 |
| J | 261 | 0.463 | 0.77 |
| K | 263 | 0.570 | 0.99 |
| L | 262 | 0.680 | 1.19 |
| M | 262 | 0.791 | 1.40 |

From the results of Table 3 and FIG. 3, it was found that the residue weight was 1 g or less in the granules I to K having a homogeneity U of 0.58 or less among the granules having an average particle diameter in a range of 207 μm to 570 μm, and the granules I to K exhibited excellent water solubility.

Production Example 3

In Production Example 3, a difference in a residue weight according to a content ratio (volume ratio) of a coarse powder having a particle diameter of 500 μm or more was confirmed.

The composition I prepared in Production Example 1 was introduced into a fluidized bed granulator together with an emulsifier as a liquid component (binder) and an aqueous solution of thickening polysaccharides, and five types of granules N to R shown in Table 4 were obtained by changing the amount of the binder to be added, a spray air flow rate, and the like.

In addition, the obtained granules N to R were evaluated for water solubility in the same manner as in Production Example 1.

Figure 4:
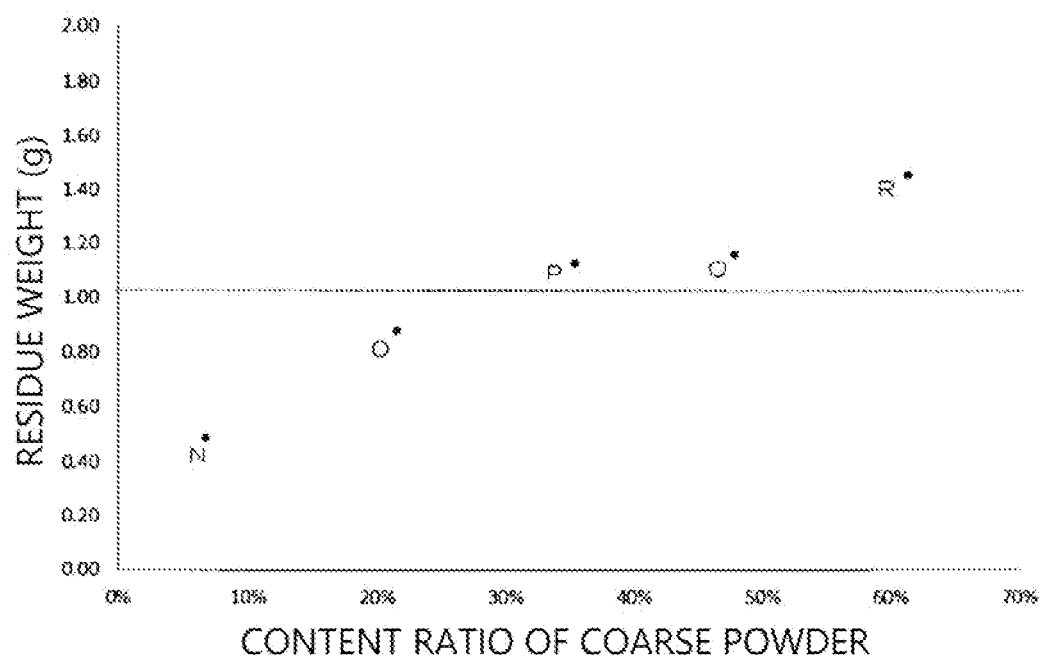
FIG. 4 is a graph illustrating a relationship between a content ratio of a coarse powder and a residue weight in Production Example 3, in which a horizontal line in FIG. 4 indicates that the residue weight is 1 g.

The results are shown in Table 4 and FIG. 4.

TABLE 4

Production Example 3

| Granule | Average particle diameter (μm) | Homogeneity U | Content ratio (%) of coarse powder (500 μm or more) | Content ratio (%) of fine powder (150 μm or less) | Residue weight (g) |
| --- | --- | --- | --- | --- | --- |
| N | 265 | 0.371 | 6.710 | 11.46 | 0.49 |
| O | 325 | 0.456 | 21.54 | 7.880 | 0.88 |
| P | 401 | 0.481 | 35.35 | 6.060 | 1.12 |
| Q | 484 | 0.449 | 47.82 | 3.700 | 1.16 |
| R | 562 | 0.331 | 61.29 | 2.670 | 1.45 |

From the results of Table 4 and FIG. 4, it was found that the residue weight was 1 g or less in the granules N and O having a content ratio (volume ratio) of the coarse powder of 22% or less among the granules having an average particle diameter in a range of 207 μm to 570 μm and a homogeneity U of 0.58 or less, and the granules N and O exhibited excellent water solubility.

Production Example 4

In Production Example 4, a difference in a residue weight according to a content ratio (volume ratio) of a fine powder having a particle diameter of 150 μm or less was confirmed.

The composition 1 prepared in Production Example 1 was introduced into a fluidized bed granulator together with an emulsifier as a liquid component (binder) and an aqueous solution of thickening polysaccharides, and four types of granules S to V shown in Table 5 were obtained by changing the amount of the binder to be added, a spray air flow rate, and the like. The granule N in Table 5 is the same as that prepared in Production Example 3.

In addition, the obtained granules N and S to V were evaluated for water solubility in the same manner as in Production Example 1.

Figure 5:
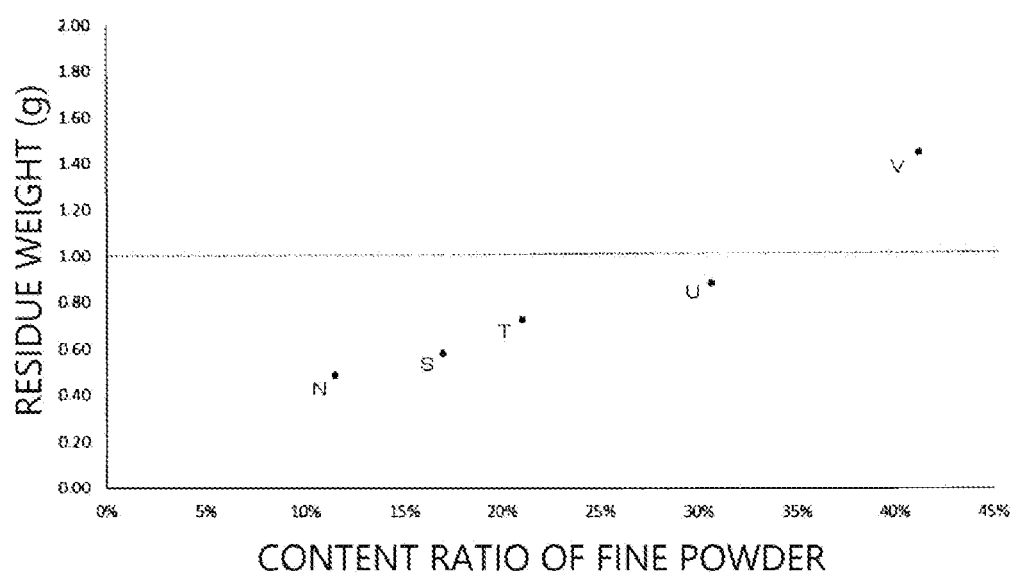
FIG. 5 is a graph illustrating a relationship between a content ratio of a fine powder and a residue weight in Production Example 4, in which a horizontal line in FIG. 5 indicates that the residue weight is 1 g.

The results are shown in Table 5 and FIG. 5.

TABLE 5

| | Production Example 4 | | | | |
|---|---|---|---|---|---|
| Granule | Average particle diameter (μm) | Homogeneity U | Content ratio (%) of fine powder (150 μm or less) | Content ratio (%) of coarse powder (500 μm or more) | Residue weight (g) |
| N | 265 | 0.371 | 11.46 | 6.710 | 0.49 |
| S | 261 | 0.463 | 16.95 | 10.48 | 0.58 |
| T | 238 | 0.429 | 20.99 | 5.350 | 0.73 |
| U | 207 | 0.502 | 30.63 | 4.900 | 0.89 |
| V | 168 | 0.401 | 41.18 | 0.070 | 1.45 |

From the results of Table 5 and FIG. 5, it was found that the residue weight was 1 g or less in the granules N and S to U having a content ratio (volume ratio) of the fine powder of 31% or less among the granules having an average particle diameter in a range of 207 μm to 570 μm and a homogeneity U of 0.58 or less, and the granules N and S to U exhibited excellent water solubility.

From the above results, it was confirmed that protein granules containing a whey protein as a main component, having an average particle diameter of 207 μm to 570 μm, a homogeneity U of 0.58 or less, a content ratio (volume ratio) of coarse powder having a particle diameter of 500 μm or more of 22% or less, and a content ratio (volume ratio) of fine powder having a particle diameter of 150 μm or less of 31% or less, exhibited sufficiently high solubility in water, and a protein solution having less undissolved protein and being easily swallowed can be prepared.

Although various embodiments have been described above with reference to the drawings, it is needless to say that the present invention is not limited to such examples. It is apparent to those skilled in the art that various changes and modifications can be conceived within the scope of the claims, and it is also understood that such variations and modifications belong to the technical scope of the present invention. In addition, constituent elements in the embodiments described above may be combined freely within a range not departing from the spirit of the present invention.

The present application is based on Japanese Patent Application No. 2019-172258 filed on Sep. 20, 2019, the contents of Which are incorporated herein by reference.

The invention claimed is:

1. Protein granules comprising a whey protein as a main component,
wherein the protein granules have an average particle diameter of 207 μm to 570 μm, a homogeneity U of 0.58 or less, a content ratio (volume ratio) of a coarse powder having a particle diameter of 500 μm or more of 22% or less, and a content ratio (volume ratio) of a fine powder having a particle diameter of 150 μm or less of 31% or less, and wherein the average particle diameter, the homogeneity U, the content ratio (volume ratio) of the coarse powder having a particle diameter of 500 μm or more, and the content ratio (volume ratio) of the fine powder having a particle diameter of 150 μm or less, are determined by the following measurement method:

1. A volume-based particle size distribution in which data is plotted with the particle diameter as a horizontal axis and with a content ratio of particles as a vertical axis is obtained for the granules by a laser diffraction and scattering measurement method, 2. The average particle diameter and the content ratio (volume ratio) of the coarse powder and the content ratio (volume ratio) of the fine powder are determined from the volume-based particle size distribution, and 3. The homogeneity U is determined by the following formula (1), $$U = \frac{\sum X_i |D_i - D_p|}{D_p} \quad (1)$$

where, in the formula (1), $D_p$ is an average particle diameter (μm), $X_i$ is a content ratio of particles at each particle diameter in the volume-based particle size distribution, and $D_i$ is a particle diameter (μm) of each particle.

2. The protein granules according to claim 1, wherein the protein granules have a protein content of 50 mass % or more.

3. The protein granules according to claim 1, wherein the protein granules have the average particle diameter of 260 μm to 330 μm.

4. The protein granules according to claim 1, wherein the protein granules have the homogeneity U of 0.36 to 0.47.

5. The protein granules according to claim 1, wherein the protein granules have the content ratio (volume ratio) of the coarse powder having a particle diameter of 500 μm or more of 11% or less, and the content ratio (volume ratio) of the fine powder having a particle diameter of 150 μm or less of 17% or less.

6. The protein granules according to claim 1, wherein a residue weight of the granules is 1 g or less, when 7 g of the granules is added to 100 ml of water and stirred to produce a mixture, then the mixture is sieved with a sieve having a size of mesh opening of 500 μm, and granules remaining on the sieve are dried at 98° C. for 4 hours.

7. The protein granules according to claim 2, wherein the protein granules have the average particle diameter of 260 μm to 330 μm.

8. The protein granules according to claim 2, wherein the protein granules have the homogeneity U of 0.36 to 0.47.

9. The protein granules according to claim 3, wherein the protein granules have the homogeneity U of 0.36 to 0.47.

10. The protein granules according to claim 7, wherein the protein granules have the homogeneity U of 0.36 to 0.47.

11. The protein granules according to claim 2, wherein the protein granules have the content ratio (volume ratio) of the coarse powder having a particle diameter of 500 μm or more of 11% or less, and the content ratio (volume ratio) of the fine powder having a particle diameter of 150 μm or less of 17% or less.

12. The protein granules according to claim 3, wherein the protein granules have the content ratio (volume ratio) of the coarse powder having a particle diameter of 500 μm or more of 11% or less, and the content ratio (volume ratio) of the fine powder having a particle diameter of 150 μm or less of 17% or less.

13. The protein granules according to claim 4, wherein the protein granules have the content ratio (volume ratio) of the coarse powder having a particle diameter of 500 μm or more of 11% or less, and the content ratio (volume ratio) of the fine powder having a particle diameter of 150 μm or less of 17% or less.

14. The protein granules according to claim 7, wherein the protein granules have the content ratio (volume ratio) of the coarse powder having a particle diameter of 500 μm or more of 11% or less, and the content ratio (volume ratio) of the fine powder having a particle diameter of 150 μm or less of 17% or less.

15. The protein granules according to claim 8, wherein the protein granules have the content ratio (volume ratio) of the coarse powder having a particle diameter of 500 μm or more of 11% or less, and the content ratio (volume ratio) of the fine powder having a particle diameter of 150 μm or less of 17% or less.

16. The protein granules according to claim 9, wherein the protein granules have the content ratio (volume ratio) of the coarse powder having a particle diameter of 500 μm or more of 11% or less, and the content ratio (volume ratio) of the fine powder having a particle diameter of 150 μm or less of 17% or less.

17. The protein granules according to claim 10, wherein the protein granules have the content ratio (volume ratio) of the coarse powder having a particle diameter of 500 μm or more of 11% or less, and the content ratio (volume ratio) of the fine powder having a particle diameter of 150 μm or less of 17% or less.

18. The protein granules according to claim 2, wherein a residue weight of the granules is 1 g or less, when 7 g of the granules is added to 100 ml of water and stirred to produce a mixture, then the mixture is sieved with a sieve having a size of mesh opening of 500 μm, and granules remaining on the sieve are dried at 98° C. for 4 hours.

19. The protein granules according to claim 3, wherein a residue weight of the granules is 1 g or less, when 7 g of the granules is added to 100 ml of water and stirred to produce a mixture, then the mixture is sieved with a sieve having a size of mesh opening of 500 μm, and granules remaining on the sieve are dried at 98° C. for 4 hours.

20. The protein granules according to claim 4, wherein a residue weight of the granules is 1 g or less, when 7 g of the granules is added to 100 ml of water and stirred to produce a mixture, then the mixture is sieved with a sieve having a size of mesh opening of 500 μm, and granules remaining on the sieve are dried at 98° C. for 4 hours.

* * * * *